United States Patent [19]

Houts

[11] Patent Number: 4,465,775

[45] Date of Patent: Aug. 14, 1984

[54] VITAMIN $B_{12}$ AND LABELLED DERIVATIVES FOR SUCH ASSAY

[75] Inventor: Thomas M. Houts, London, England

[73] Assignee: Technicon Instruments Corporation, Tarrytown, N.Y.

[21] Appl. No.: 381,267

[22] Filed: May 24, 1982

[30] Foreign Application Priority Data

Jun. 22, 1981 [GB] United Kingdom ................. 8119147

[51] Int. Cl.$^3$ ...................... G01N 33/60; G01N 33/82; G01N 33/50; C08G 77/04
[52] U.S. Cl. ..................................... 436/503; 536/25; 435/4; 435/14; 435/21; 435/25; 436/504; 436/544; 436/545; 436/546; 436/505
[58] Field of Search ............................. 424/1, 1.5, 1.1; 23/230 B, 230 R; 436/501–505, 546, 545, 544, 804, 815, 825; 435/4, 14, 21, 25; 260/112 R, 112 T; 536/25

[56] References Cited

U.S. PATENT DOCUMENTS

| | | | |
|---|---|---|---|
| 3,981,863 | 9/1976 | Niswender et al. | 436/505 |
| 3,989,812 | 11/1976 | Barrett et al. | 436/505 |
| 4,091,087 | 5/1978 | Barrett et al. | 436/505 |
| 4,209,614 | 6/1980 | Bernstein et al. | 436/505 |
| 4,276,280 | 6/1981 | Akerkar et al. | 436/505 |
| 4,298,735 | 11/1981 | Farina et al. | 436/505 |
| 4,336,185 | 6/1982 | Niswender | 436/505 |

OTHER PUBLICATIONS

Endres, D. B. et al., Clin. Chem., vol. 24 (3), pp. 460–465, (1978).

Armitage, J. B. et al., J. Chem. Society, pp. 3849–3864, (1953).

Houts, T. M., Clinica Chimica Acta (1982), pp. 315–322, (1982).

Anton, D. L. et al., J. Am. Chem. Soc., vol. 102 (7), pp. 2215–2219, (1980).

Houts, T. M. et al., Clin. Chem., vol. 27 (2), pp. 263–267, (1981).

Lau, K. S. et al., Blood, vol. 26 (2), pp. 202–214, (1965).

Erlanger, B. F. et al., J. Biol. Chem., vol. 228, pp. 713–727, (1957).

Kolhouse et al., Journal Clinical Investigation, vol. 60, pp. 1381–1392, (1977).

Yamada et al., Journal Biological Chemistry, vol. 247, pp. 6266–6270.

*Primary Examiner*—Benjamin R. Padgett
*Assistant Examiner*—M. Moskowitz
*Attorney, Agent, or Firm*—S. P. Tedesco; C. J. Herron

[57] ABSTRACT

Vitamin $B_{12}$ in liquid samples, such as human serum or human plasma, is assayed by a competitive binding technique using intrinsic factor and certain labelled vitamin $B_{12}$ derivatives. The labelled derivatives are formed from the (d)-monocarboxylic acid isomer of vitamin $B_{12}$, which isomer is free from other monocarboxylic acid isomers (and derivatives thereof) of vitamin $B_{12}$, by binding to the (d)-isomer, via the carboxylic group, a compound which is itself a label (e.g. an enzyme) or which comprises a label (e.g. a fluorophore), or to which a label is attached (e.g. a histidine ester to which $^{125}I$ is attached). The labelled derivatives of the (d)-monocarboxylic acid of vitamin $B_{12}$, free from other isomeric monocarboxylic acids and derivatives, are novel and constitute one aspect of the invention.

14 Claims, 2 Drawing Figures

VITAMIN $B_{12}$ AND LABELLED DERIVATIVES FOR SUCH ASSAY

This invention is concerned with the assay of vitamin $B_{12}$ and with certain labelled derivatives of vitamin $B_{12}$ which are useful in such an assay.

The classic assay for vitamin $B_{12}$ (hereinafter for brevity referred to simply as "$B_{12}$") is a microbiological assay utilising, for example, *E. gracilis*. Whilst this assay is widely accepted as accurate and reliable, it is a relatively slow method involving manual techniques. In recent years, attempts have been made to devise alternative procedures based on the well known competitive binding reaction technique, with a view to providing a quicker and equally reliable assay.

Assays based on competitive binding advantageously employ a labelled reactant, i.e. a reactant which carries an atom or group which can readily be identified and assayed. Commonly used labels include radioactive atoms, and fluorescent or enzymic groups. There have been various proposals for making a radioactively labelled $B_{12}$ derivative for use in a competitive binding assay of $B_{12}$. One proposal, which is used commercially, involves the incorporation of $^{57}Co$ in the biosynthesis of $B_{12}$. This is a complicated process and the $^{57}Co$-$B_{12}$ produced is expensive. Furthermore, the specific activity of the product is relatively low (220 $\mu Ci/\mu g$) which, in turn, necessitates relatively lengthy counting times (of at least one minute) in competitive binding assays using this $^{57}Co$-$B_{12}$. Low activity and long counting times are highly undesirable.

Another approach has been to prepare $^{125}I$-$B_{12}$ derivatives. U.S. Pat. No. 4,209,614 describes the preparation of such derivatives by reacting $B_{12}$ with a glutaric anhydride derivative (which binds to the $B_{12}$ via its sugar ring), and then iodinating the glutaric anhydride derived substituent.

A further process for preparing $^{125}I$-$B_{12}$ derivatives is described in U.S. Pat. No. 3,981,863. In this process, $B_{12}$ is first subject to mild hydrolysis to form a mixture of monocarboxylic acids containing mostly the (e)-isomer. (The structure of vitamin $B_{12}$ is shown in FIG. 1 of the accompanying drawings.) The mixture is then reacted with a p-(aminoalkyl)phenol to introduce a phenol group into the $B_{12}$ acids (via reaction with one of the free carboxylic acid groups). The mixed substituent $B_{12}$ derivatives are then iodinated in the phenol-group substituent. This U.S. patent teaches that the mixed $^{125}I$-$B_{12}$ derivatives so made are useful in the radioimmunoassay of $B_{12}$, using antibodies raised against the mixture.

It has recently become clear (see, for example, PCT patent application U.S. No. 79/00210, published as WO No. 79/00880) that in competitive binding assays of $B_{12}$, the nature of the binding protein used is of critical importance. In particular, it has been found that some binding proteins whose use has previously been suggested, not only bind to $B_{12}$ but also to cobalamin analogues. For example, it has been shown that transcobalamin II and R proteins bind to $B_{12}$ and also to cobalamin analogues present in human sera. This lack of specificity leads to erroneous assay results. It is now generally accepted that the best binding protein to use is intrinsic factor (hereinafter "IF"), since this is highly selective for the physiologically active form of $B_{12}$ in human sera. There is a requirement therefore for a labelled-$B_{12}$ derivative which will bind strongly with IF.

We have investigated the mixture of $^{125}I$-$B_{12}$ derivatives described in U.S. Pat. No. 3,981,863 but have found that the mixture is not suitable for use in $B_{12}$ assays utilising IF. The mixture is suitable (as described in the patent) where antibodies raised against the mixture are used as the binding protein, but when instead IF is used as the binding protein the assay is not accurate. We have further found that the reason for this is that the different components of the mixture surprisingly have markedly different affinities for IF. In fact we have found that, of the derivatives, those of the monocarboxylic-(d)-isomer have a very much greater affinity for IF than do the (b)- or (e)-isomer derivatives. This finding is, incidentally, in line with results reported in a paper by Kolhouse and Allen (J. Clin. Invest. 60, 1381–1392) which is not concerned with $B_{12}$ analysis but reports the following affinities for rabbit and human IF of the three monocarboxylic acids:

| Monocarboxylic Acid Isomer | $\frac{Ka\ B_{12}\text{—COOH isomer}}{Ka\ Cyanocobalamin}$ |
|---|---|
| (b) | 0.0006 |
| (d) | 0.3 |
| (e) | 0.004 |

These affinities relate, of course, to the free acids but we have found that generally the same order of affinities is found in the derivatives thereof.

Accordingly, we have found that derivatives of the (d)-isomer, suitably radioactively labelled, are appropriate for use in assays of $B_{12}$ in which IF is used. It is an important aspect of the present invention that labelled (d)-derivatives are used which are pure or, at least, substantially free from (b)- or (e)-isomer derivatives, since the presence of (b)- or (e)-isomer derivatives will lead to anomalous results.

The labelled derivatives of the purified $B_{12}$ (d)-acid isomer are novel and, accordingly, in one aspect the invention provides labelled derivatives of the monocarboxylic (d)-isomer of $B_{12}$, in which a labelled group is bound to the (d)-carboxylic acid group, which isomer or derivative is free from other monocarboxylic acid isomers of $B_{12}$ and derivatives made therefrom.

In another aspect, the invention provides a method of assaying $B_{12}$ in a sample which comprises forming a competitive binding mixture of the sample with IF and a labelled derivative of the (d)-monocarboxylic isomer of $B_{12}$, in the absence of any other monocarboxylic isomer of $B_{12}$ or derivative made therefrom. If the method of assay involves a boiling step (which is usual but is not always necessary—see our U.K. patent specification No. 2011070 the labelled (d)-isomer should be added to the reaction mixture only after the boiling step has been completed.

The drawings are briefly described as follows.

Figure 1:
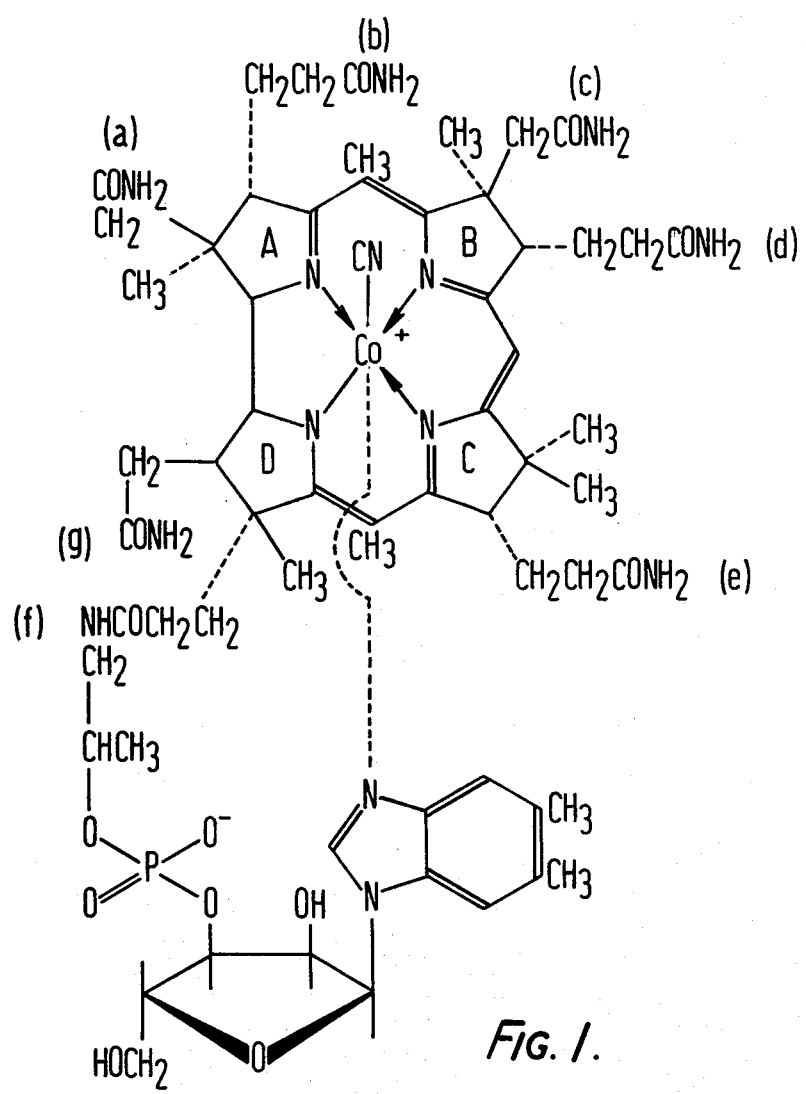
FIG. 1 is an illustration of the chemical structure of cyanocobalamin (vitamin $B_{12}$).

The labelled derivatives of the (d)-acid isomer are made by coupling to the (d)-acid group a further group which already carries, or may subsequently have attached thereto, a label. The preferred types of iodine receptors for coupling to the (d)-isomer monocarboxylic acid of $B_{12}$ according to this invention are as follows:

(1) p-aminoalkylphenols such as tyramine with the general structure

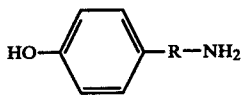

where R is an alkylene group having from 1 to 18 carbon atoms (see U.S. Pat. No. 3,981,863).

(2) alkyl esters of tyrosine such a tyrosine methyl ester and having the general structure

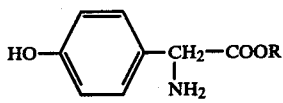

where R is an alkyl group having from 1 to 18 carbon atoms.

(3) aminoalkylimidazoles such as histamine with the general structure

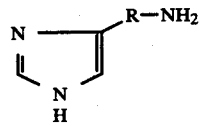

where R is an alkylene group having from 1 to 18 carbon atoms.

(4) alkyl esters of histidine such as histidine methyl ester with the general structure

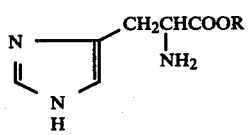

where R is an alkyl group having from 1 to 18 carbon atoms.

Derivatives of the present invention comprising iodine receptors of type 1 or 2 above are made by the method described in U.S. Pat. No. 3,981,863 (except of course that the (d)-monocarboxylic acid of $B_{12}$ is used alone). The teachings of the said U.S. Pat. No. 3,981,863 are incorporated herein by reference. Those derivatives of the invention with iodine receptors of type 3 and 4 are made as described in the Example hereinafter.

The label may be a radioactive atom such as $^{125}I$, or it may be a fluorophore or an enzyme or other label. A fluorescent-labelled isomer may be made, for example, by reacting the (d)-isomer monocarboxylic acid of $B_{12}$, substantially free of the (b)- and (e)-isomers, with a fluorophore, for example fluoresceinthiocarbamyl ethylene diamine. An enzyme-labelled isomer may be made, for example, by reacting a (d)-isomer monocarboxylic acid of $B_{12}$, substantially free of the (b)- and (e)-isomers, with an enzyme, for example beta-galactosidase to give an enzymically labelled derivative of $B_{12}$. Other commonly used enzymes which could be used for this purpose include horseradish peroxidase and alkaline phosphatase.

In order to prepare the pure (d)-monocarboxylic acid isomer, $B_{12}$ is first subjected to mild acid hydrolysis as described in U.S. Pat. No. 3,981,863 (see also J.C.S. (1953), 3848–3864). This results in the formation of a mixture of three monocarboxylic acids, namely the (b), (d) and (e) isomers. Typically, the mixture comprises 50% (e)-isomer, 25% (b)-isomer and 25% (d)-isomer. The (d)-isomer is then separated from the other isomers by the method described by Yamada et al (J. Biol. Chem., 247, 6266–6270). The identity of each of the separated isomers can be confirmed by paper chromotography using the method described by Allen et al (J. Clin. Invest. (1977) 60, 1381–1392).

In order that the invention may be more fully understood, the following Example is given by way of illustration only.

EXAMPLE

Preparation of monocarboxylic acids

The individual isomers were prepared and purified by the method of Yamada and Hogenkamp (J. Biol. Chem. 247, 6266–6270). The identity of the isomers was confirmed by paper chromatography (J. Clin. Invest. 60, 1381–1392).

Preparation of histamine conjugates

The carboxylic acids were conjugated to histamine via an isobutylchloroformate intermediate (see Erlanger, Boreck, Beiser and Lieberman, *J. Biol. Chem.*, 228, 713 (1957)). After the reaction, the corrinoids were precipitated by addition of acetone, the precipitate redissolved in water and the unreacted carboxylic acid removed by passing over a 0.7×10 cm column of Dowex AG1-X2 acetate. Unreacted histamine was removed by extraction into phenol and backextraction into water (see Kolhouse and Allen, *Analyt. Biochem.* 84, 486–490 (1978)). Finally the last traces of phenol were removed by adjusting the pH to 10 with concentrated ammonium hydroxide solution and passing over a 0.7×10 cm column of Dowex AG1-X2 acetate. The solution was neutralised with acetic acid and stored at −20° C.

Iodination of histamine conjugates

The cobalamin-histamide conjugates were calibrated spectrophotometrically at 361 nm using a molar extinction coefficient of 27,700 and diluted to 50 μmol/L in 0.1 mol/L phosphate buffer, pH 7.5. 10 μl (0.5 nmol) of the conjugate solution was added to 20 μL (2 mCi, 1 nmol) of Na$^{125}$I followed by 10 μL chloroamine-T solution (1 g/L). After 5 min the reaction was stopped by the addition of 10 μl sodium metabisulphite solution (1.9 g/L). Unreacted iodide was removed by batch treatment with 50 μl Dowex AG1-X2 acetate and the resin washed with water. The iodinated product was diluted to a concentration of 100 μg/L (based on starting concentration) in water containing 9 g/L benzyl alcohol stored at 4° C. Incorporation of $^{125}$I ranged from 41% to 55% in 8 separate iodinations, giving specific activities in the range 1200–1600 Ci/g.

Binding properties of the iodinated conjugates

The iodinated materials and [$^{57}$Co] cyanocobalamin were tested for their ability to bind to a 10-fold excess of anti-$B_{12}$ serum prepared as described in U.S. Pat. No. 3,981,863 and to a 10-fold excess of IF under assay conditions (see below). The results are summarised in Table 1. This demonstrates that, while all three isomers are suitable for use with antibodies prepared as in U.S.

Pat. No. 3,981,863, only the (d)-isomer is suitable for use with IF.

Figure 2:
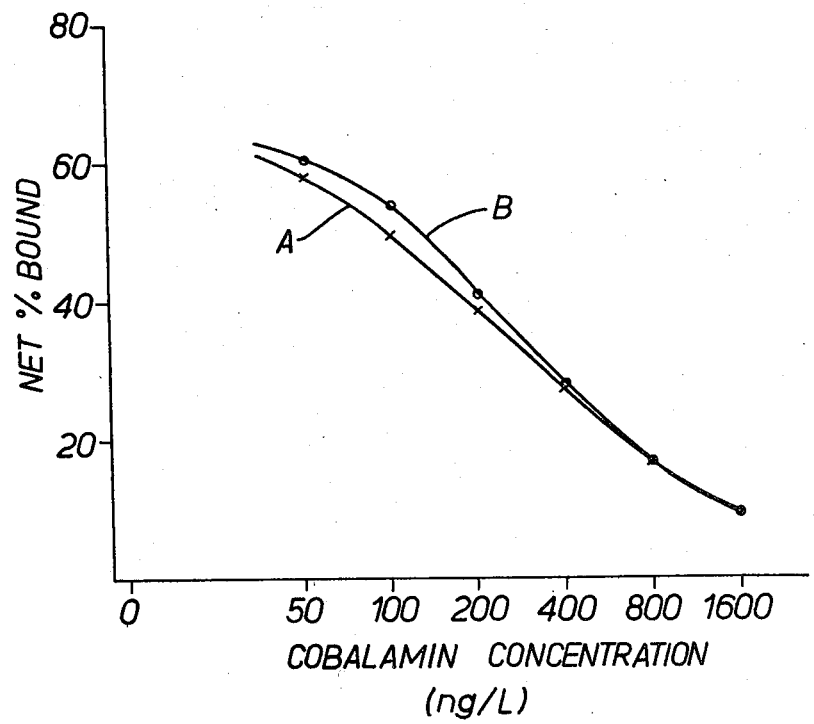
FIG. 2 is a graphical representation of the data in Table 1 of the comparative example.

Comparison of [57Co] cyanocobalamin and [125I] cyanocobalamin-d-iodohistamide in competitive protein binding assay Intrinsic factor (<2% R-protein, from Sigma Chemicals) was dissolved in borate buffer (50 mmol/L, pH 9.5 containing 1 g/L HSA) to a concentration of 1 unit/mL. The tracers were each diluted to 50 ng/L in borate buffer containing 1 g/L dithioerythritol and 50 mg/L KCN. Each assay tube contained 0.2 mL cyanocobalamin standard, 1 mL tracer, and 0.1 mL IF. Maximum binding was determined by adding 0.1 ml IF at a concentration of 10 units per mL. Non-specific binding was determined by adding buffer instead of IF. After incubation at room temperature for 1 hr, 0.5 mL albumin-coated charcoal was added. After centrifuging for 10 min at 1500 g the supernates were decanted into tubes and counted. The standard curves, corrected for maximum and non-specific binding from table 1 are shown in FIG. 2, in which curve A is that for [57Co]-cyanocobalamin tracer and curve B is that [125I] cyanocobalamin d-iodohistamide as tracer.

In the method of assay of the invention, the binding protein is preferably pure IF. However, the binding protein may be a mixture of IF and R-protein, in which mixture the R-protein has been inactivated by digestion or by $B_{12}$ analogues which inactive the R-protein binding sites.

TABLE 1

Binding of labelled $B_{12}$ (histamine conjugate) to antiserum and to purified intrinsic factor

| | Using anti-$B_{12}$ serum | | Using purified intrinsic factor | |
|---|---|---|---|---|
| | Max binding % | NSB % | Max binding % | NSB % |
| 57Co-$B_{12}$ | 92.1 | 7.5 | 91.7 | 2.8 |
| 125I-$B_{12}$-b-iodohistamide | 86.5 | 3.8 | 11.3 | 5.2 |
| 125I-$B_{12}$-d-iodohistamide | 88.2 | 5.8 | 81.2 | 5.3 |
| 125I-$B_{12}$-e-iodohistamide | 88.1 | 4.6 | 28.2 | 4.4 |

I claim:

1. A derivative of vitamin $B_{12}$ which includes an identifying label whereby the said derivative can be used in a competitive binding assay for vitamin $B_{12}$ and quantitated by measurement of said label, wherein the said derivative is prepared from the (d)-monocarboxylic acid isomer of vitamin $B_{12}$ and comprises a labelled group bound to the (d)-carboxylic acid group, the derivative being free from other monocarboxylic acid isomers of vitamin $B_{12}$ and derivatives thereof.

2. A derivative according to claim 1, wherein the labelled group contains a radioactive atom.

3. A derivative according to claim 2, wherein the radioactive atom is 125I.

4. A derivative according to claim 1, wherein the labelled group is formed by binding to the (d)-carboxylic acid group, a compound selected from:

(a) a p-aminoalkylphenol with the general structure:

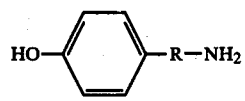

where R is an alkylene group having from 1 to 18 carbon atoms;

(b) an alkyl ester of tyrosine having the general structure:

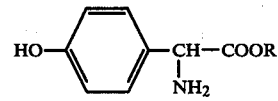

where R is an alkyl group having from 1 to 18 carbon atoms;

(c) an aminoalkylimidazole with the general structure:

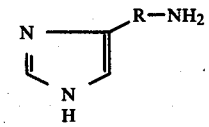

where R is an alkylene group having from 1 to 18 carbon atoms; and (d) an alkyl ester of histidine with the general structure:

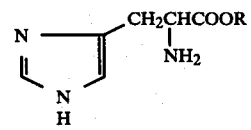

where R is an alkyl group having from 1 to 18 carbon atoms;

and wherein 125I is introduced into the said compound before or after binding the compound to the (d)-carboxylic acid group.

5. A derivative according to claim 1, wherein the labelled group comprises a fluorophore.

6. A derivative according to claim 5, wherein the labelled group is formed by reacting the (d)-carboxylic acid group with fluoresceinthiocarbamyl ethylene-diamine.

7. A derivative according to claim 1, wherein the labelled group comprises an enzyme.

8. A derivative according to claim 7, wherein the labelled group is formed by reacting the (d)-carboxylic acid group with an enzyme selected from beta-galactidose, horseradish peroxidase and alkaline phosphatase.

9. A method of making a labelled derivative of vitamin $B_{12}$, which comprises subjecting vitamin $B_{12}$ to mild acid hydrolysis to form a mixture of monocarboxylic acid isomers thereof; separating the (d)-isomer from the other isomers; reacting the separated (d)-isomer via its (d)-monocarboxylic acid group with a compound which is selected from (1) compounds which are labels, (2) compounds which comprise a label, and (3) compounds to which a label may subsequently be bound; and in case (3) thereafter binding a label thereto.

10. A method of assaying vitamin $B_{12}$ in a liquid sample which comprises forming a competitive binding mixture of the sample with intrinsic factor and a labelled derivative of vitamin $B_{12}$, and measuring the bound or free label and therefrom determining the vitamin $B_{12}$ in the sample, wherein the labelled derivative of vitamin $B_{12}$ is prepared from the (d)-monocarboxylic acid isomer of vitamin $B_{12}$ and comprises a labelled group bound to the (d)-carboxylic acid group, the derivative being free from other monocarboxylic acid isomers of vitamin $B_{12}$ and derivatives thereof.

11. A method according to claim 10, wherein the labelled group is formed by binding to the (d)-carboxylic acid group, a compound selected from:

(a) a p-aminoalkylphenol with the general structure:

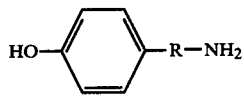

where R is an alkylene group having from 1 to 18 carbon atoms;

(b) an alkyl ester of tyrosine having the general structure:

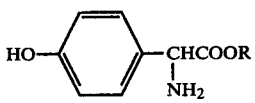

where R is an alkyl group having from 1 to 18 carbon atoms;

(c) an aminoalkylimidazole with the general structure:

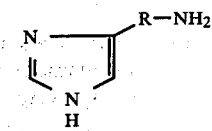

where R is an alkylene group having from 1 to 18 carbon atoms; and (d) an alkyl ester of histidine with the general structure:

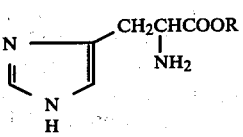

where R is an alkyl group having from 1 to 18 carbon atoms;
and wherein $^{125}I$ is introduced into the said compound before or after binding the compound to the (d)-carboxylic acid group.

12. A method according to claim 10, which includes the preliminary step of boiling the sample to denature endogenous vitamin $B_{12}$ binding proteins therein, and wherein the said labelled derivative is mixed with the sample after the latter has been boiled.

13. A method according to claim 10, wherein the sample is selected from human serum and human plasma.

14. A substantially pure radioactively labelled derivative of vitamin $B_{12}$ which can be used in a competitive binding assay for vitamin $B_{12}$ to bind with intrinsic factor, the said derivative consisting of the product of reaction between the (d)-carboxylic acid group of the (d)-monocarboxylic acid isomer of vitamin $B_{12}$ and a compound selected from tyramine, tyrosine methyl ester, histamine and histidine methyl ester, the said derivative including at least one $^{125}I$ atom substituent in the said compound.

* * * * *